United States Patent
Baudino

(10) Patent No.: US 6,185,463 B1
(45) Date of Patent: Feb. 6, 2001

(54) IMPLANTABLE SHORT RESISTANT LEAD

(75) Inventor: Michael D. Baudino, Coon Rapids, MN (US)

(73) Assignee: Medtronic, Inc., Minneapolis, MN (US)

( * ) Notice: Under 35 U.S.C. 154(b), the term of this patent shall be extended for 0 days.

(21) Appl. No.: 08/848,794

(22) Filed: May 1, 1997

(51) Int. Cl.[7] .................................................. A61N 1/04
(52) U.S. Cl. .............................................................. 607/119
(58) Field of Search .................................. 607/119, 117, 607/122

(56) References Cited

U.S. PATENT DOCUMENTS

| | | | |
|---|---|---|---|
| 3,724,467 | 4/1973 | Avery et al. | 128/418 |
| 3,995,623 | 12/1976 | Blake et al. | 128/2.06 E |
| 4,379,462 | 4/1983 | Borkan | 128/786 |
| 4,437,474 | 3/1984 | Peers-Trevarton | 128/784 |
| 4,458,695 | 7/1984 | Peers-Trevarton | 128/786 |
| 4,592,372 | 6/1986 | Beranek | 128/786 |
| 4,608,986 | 9/1986 | Beranek | 128/786 |
| 4,633,889 | * 1/1987 | Talalla et al. | 607/117 |

OTHER PUBLICATIONS

Medtronic Model 3487 A Pisces Quad™ Lead.

* cited by examiner

Primary Examiner—Scott M. Getzow
(74) Attorney, Agent, or Firm—Curtis D. Kindhorn; Harold R. Patton

(57) ABSTRACT

The present invention is a body implantable medical lead and method for constructing the lead. The lead has at least one electrode located along the lead body that is recessed from the outer surface of the lead body. The recessed electrode helps to prevent contact between the electrode and electrodes on a different lead when the different leads are brought into contact with each other.

61 Claims, 3 Drawing Sheets

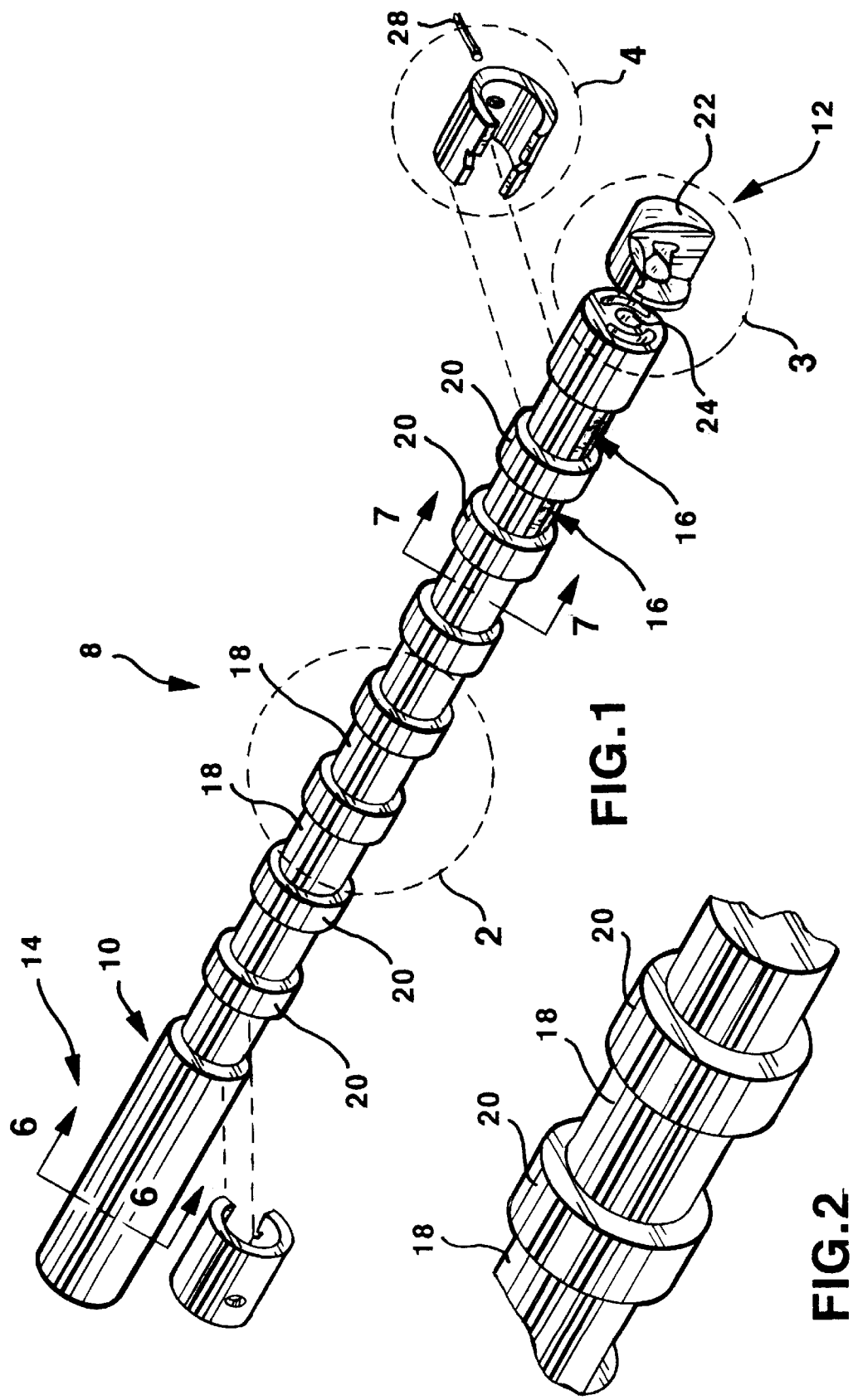

IMPLANTABLE SHORT RESISTANT LEAD

1. FIELD OF THE INVENTION

The present invention relates to a method and apparatus for providing a medical body implantable lead having a series of electrodes at its distal end which lead is resistant to "shorting" between the electrodes when the lead comes into contact with another medical body implantable lead.

2. DESCRIPTION OF THE PRIOR ART

The state of the art of implantable pulse generator and lead systems for stimulating human tissue has advanced to the point that such devices are being designed and used in increasing numbers to treat a wide variety of medical conditions. In addition to implantable pulse generator and lead systems for treating many different types of cardiac conditions (bradycardia, tachycardia, fibrillation, and the like), so called neurological pulse generator and lead systems have been provided for stimulating tissue in a patient's nervous system, in order to treat such diverse conditions as pain, motor impairment, incontinence, and impotence, to name only a few.

In most cases, electrical stimulation pulses are conveyed from an implanted pulse generator to the desired stimulation site by means of an implanted lead having exposed electrodes at its distal end. Typically, implantable spinal cord leads contain multiple electrodes. Two basic styles are available.

One style is the percutaneously inserted lead which is introduced through a Touhy needle. The implanting physician places the electrode in an appropriate location using fluoroscopic visualization. The procedure is done under a local anesthetic. Proper electrode placement is tested using a trial stimulation screening technique to assure that paresthesia is perceived in the affected area. An example of this type of lead is disclosed in U.S. Pat. No. 4,379,462 issued to Borkan.

A typical lead configuration of this percutaneous lead includes an insulated and flexible conductor having a circular cross section that is fitted with one or more ring electrodes. These ring electrodes usually have an the outer surface that is isodiametric with respect to the remainder of the lead. The isodiametric configuration minimizes the difficulty in passing the lead through a vein or through tissue. The smooth surface also minimizes the formation of potentially harmful thrombi when the lead is implanted.

That lead is designed to be inserted so that the electrodes lie inline along the spinal cord. Percutaneously inserted leads of this type provide focused stimulation patterns and are generally suited for unilateral pain problems. If the pain is bilateral it is often necessary to implant two leads, one on each side of the midline of the spinal cord. Both leads may be connected to one pulse generator or each lead may be connected to one of two separate pulse generators.

Isodiametric construction has been achieved in different ways. For example, Beranek, U.S. Pat. No. 4,592,372, discloses achieving an isodiametric configuration of an electrode assembly in a cardiac pacing lead by compressing a metallic sleeve which constitutes the ring electrode just far enough so that its outer diameter is the same as the outer diameter of the flexible body of the lead itself. Blake, et al., U.S. Pat. No. 3,995,623, proposes a construction for a lead useful in cardiac monitoring and temporary transvenous pacing which has multiple ring electrodes. Those ring electrodes are constructed from a coil strip of spring metal which appears to be crimped upon the electrode body with overlapping ends of the strip being joined to secure the ring electrode.

Beranek, U.S. Pat. No. 4,608,986, discloses a multiple lumen pacing lead having multiple ring electrodes. Although there appears to be minimal disclosure concerning the actual method of construction of the ring electrode, it would appear from the drawings that one of the crimping techniques discussed in the above patent is used to accomplish the construction.

In Peers-Trevarton, U.S. Pat. Nos. 4,437,474 and 4,458,695 a multipolar pacing lead construction having multiple ring electrodes in an isodiametric arrangement is again disclosed. In that construction, the ring electrodes appear to be received in annular slots formed between a series of insulators which are passed over the coiled conductor of the lead and presumably cemented in place with the spaces between these insulating elements defining the slots or annular spaces for the ring electrodes.

Likewise it has been known in the prior art to build an isodiametric lead with spaced ring electrodes by cementing or gluing short sections of precut tubing onto a lead body using the appropriate adhesives and using cylindrically shaped ring electrodes that are isodiametric with the tubing as the ring electrodes. Medtronic, Inc., the assignee of this application, has offered for sale a lead for spinal cord stimulation, the Model 3487A lead, fabricated in such a manner. Conductors from within the lead body can be led through to the underside of the ring electrodes and attached to the electrodes with a laser weld. Such a construction method is labor intensive and costly.

The Model 3487A lead utilizes a coiled conductor set to traverse the lead and provide the electrical path between the ring electrodes at the distal end of the lead and the connector block which connects the lead to the stimulator device. Such coiled conductors have long been used for such applications. However, improvements in noncoiled types of conductor wire afford various benefits including improved resistance to flex fatigue, improved flexibility, and better crush resistance. It has also been understood in the art that ring electrodes and isodiametric leads can be constructed with a multiple lumen interior with conductors from the various lumens being passed through the insulation covering the lead body to make contract with the underside of electrodes along the lead body, typically ring electrodes.

The second basic spinal cord stimulation lead type are commonly called "paddle" leads since they typically have a flat planar shape that resembles a paddle. This type of lead is usually surgically implanted through a laminotomy. An example of this type of "paddle" lead is the RESUME® lead manufactured by Medtronic, Inc. of Minneapolis, Minn., the assignee of the present invention. This lead has four axially aligned inline electrodes located on the outer surface of an elongate paddle at the distal end of the lead. The lead is normally implanted so that the electrodes are aligned with and lie over the midline of the spinal cord. Because leads of this type are surgically implanted, the size of the electrodes may be made larger than those of the percutaneously implanted leads.

With this type lead, various electrode combinations may be selected so that the area of stimulation may be moved along the midline of the spinal cord. The lead provides a broader stimulation pattern more suitable for midline and bilateral pain problems than the percutaneously inserted lead. An example of a surgically implanted lead is disclosed in U.S. Pat. No. 3,724,467 issued to Avery et al.

A problem with isodiametric electrodes occurs when using two or more isodiametric or paddle leads in any combination in a side by side arrangement. When two or more leads having electrodes on their outer surfaces are placed near each other, contact between an electrode on one lead and an electrode on another lead may cause one or both of the electrodes to be "shorted." In other words, the electrodes on two different leads contact each other and become electrically "common."

This "shorting" manifests itself in different ways depending on the type of implantable pulse generator used. For example, in a two channel constant voltage device where the two channels are alternately activated, touching electrodes have the effect of doubling the surface area of each electrode. This results in a reduction in impedance. Since the implantable pulse generator is programmed to maintain a constant voltage, more current will flow from the electrode and the patient will feel a stronger stimulation.

In a two channel constant voltage device where the two channels are simultaneously activated, if the touching electrodes are both active, then they would be affected by the respective voltage levels and polarities in an additive or subtractive manner. As a result, the current flow from the electrodes would be affected in an unintended manner.

Two channel devices may also be constant current devices. Constant current devices may also have the two channels activated alternately. In such a case, since the device is controlling the current, as the electrode area changes due to the contact, the voltage will be adjusted accordingly to compensate. The patient should not feel any difference.

In a two channel constant current device where the two channels are simultaneously activated, the effect will be similar to the constant voltage case simultaneously activated channels case described above. The stimulation effect in such a case could be affected in a negative manner if the channels are programmed to different values. This negative stimulation effect could manifest itself in either higher or lower stimulation sensation.

These problems are in need of a solution.

SUMMARY OF THE INVENTION

The present invention is a body implantable medical lead and method for constructing the lead. The lead has at least one electrode located along the lead body that is recessed from the outer surface of the lead body. The recessed electrode helps to prevent contact between the electrode and electrodes on a different lead when the different leads are brought into contact with each other.

In the construction method, the outer layer of insulation forming the lead body is etched or notched, for example, by being laser etched or physically milled to provide a recess in the lead insulation. This recess has a depth greater than the thickness of the ring electrode intended to be provided at that location.

An electrically conductive "C" shaped ring electrode is introduced onto the notched section on the lead by moving the notched section into the open part of the "C" shaped electrode. The "C" shaped electrode is subsequently formed into a cylindrical shape by closing the "C" shaped electrode so that the opposing edges of the "C" shaped electrode are brought to an abutting relationship.

A single conductor is brought through the insulation and aligned with a hole on the "C" shaped electrode to be welded to the electrode, for example, by laser welding. The final affixation procedure involves laser welding the abutting surfaces of the electrode together, thereby securely forming a ring electrode recessed within the notch on the lead.

By introducing a number of such "C" shaped electrodes on the lead in spaced notches and affixing them as described above, a multiple electrode lead is produced. The individual conductors attached to the affixed electrodes can be bundled, as for example as stranded wire, to produce the desirable characteristics of superior flexibility, crush resistance, and resistance against flexure fatigue.

This technique of construction, moreover, improves the efficiency of manufacture and renders possible the manufacture of a multiple electrode lead having, for example, as many as eight or more ring electrodes, with significantly reduced cost.

There is also provided in accordance with this invention a neural stimulation lead having a first lumen, which may be an axial lumen, for receiving a stiffening stylet for use during lead placement and at least one other lumen containing from four to as many as eight or more bundled stranded wire conductors each of which make electrical contact with a single ring electrode on the distal portion of the lead. The lead is also characterized by isodiametric construction featuring laser welded ring electrodes placed in notches in the lead insulation having a depth generally corresponding to the thickness of the ring electrodes.

BRIEF DESCRIPTION OF THE DRAWINGS

FIG. 1 is an isometric view of the distal portion of a neurological lead in accordance with the instant invention showing locations for eight ring electrodes. FIG. 1 illustrates the most distal ring electrode welded in place and the most proximal ring electrode about to be assembled on the lead body.

FIG. 2 is an enlargement of a midsection of the distal portion of the lead in FIG. 1 designated by the numeral 2 and showing in greater detail the notches formed on the lead to receive the ring electrodes.

DESCRIPTION OF THE PREFERRED EMBODIMENTS

Figure 4:
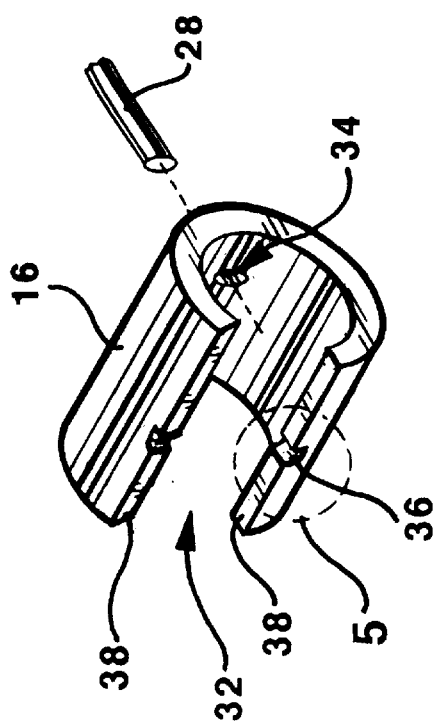
FIG. 4 is an enlargement of the area 4 of FIG. 1 and shows in detail a ring electrode construction prior to its assembly onto the lead.

The following description of the instant invention will be made in the context of the multi-electrode neurological lead illustrated in the drawings. However, it will be apparent that the concepts and principles of this invention may be applied to other stimulating leads, and furthermore can be applied to the construction of ring electrodes for leads useful in other applications such as pacing leads and electrophysiologic recording leads.

FIG. 1 shows a neural stimulator lead generally labeled 8. Lead 8 has a lead body 10, a distal end 12 and a proximal end 14. As can be seen, a series of electrodes 16 extends along the distal end 12 of lead 8. In the embodiment shown, the number of electrodes 16 is eight.

The ultimate proximal end 14 of the lead 8 (not illustrated) extends to the an implantable electrical pulse generator such as an Itrel II Implantable Pulse Generator (IPG) offered for sale by Medtronic, Inc. of Minneapolis, Minn. Other pulse generators, implanted, external or Radio-Frequency may be used in place of the Itrel II model.

Proximal end 14 terminates in a series of ring contacts that may be connected to a connector block of a type well known in the art. In connection with the embodiment shown, such a connector block will include eight set screws adapted to engage the ring contacts at the proximal end 14 of lead 8. Each ring contact is in electrical communication with one of the electrodes 16 at the distal end 12 of lead 8 thereby establishing discrete electrical paths from the IPG to deliver a stimulating signal to each ring electrode separately. The ring contacts may be constructed in a manner similar to that described with respect to the electrodes 16 as will be described in detail hereafter.

The distal end 12 of lead 8 is provided with eight notches 18. Notches 18 may be produced means such as by physically milling insulation from the surface of lead 8 or by laser etching the insulation off lead 8. Other techniques for producing notches 18 will occur to those skilled in the art. The technique for making notches 18 is not critical so long as a notch of accurate and controlled dimension, as will be described hereafter, can be produced. The notches form annular troughs around the lead body 10.

Between and on both sides of notches 18, lands 20 separate electrodes 16. Lands 20 are preferably the original insulating material of the lead 8. Alternately, lands 20 may be formed of generally cylindrical insulating sleeves cemented in place around a central core. Lands 20 are positioned above the notches 18 by an amount greater than the thickness of the electrode 16. A typical thickness for an electrode 16 is about 0.005 inch. Therefore, when using electrodes 16 having a thickness of about 0.005 inch, lands 20 should be positioned more than 0.005 inch above the notches. A difference in height between the outer surface of electrode 16 and the adjoining land 20 of about 0.005 inch is preferred. So, for a lead 8 having an outer diameter of 0.050 inch, the diameter of the outer surface of an electrode 16 would preferably be 0.040 inch.

Although specific dimensions have been given to illustrate the invention, it is to be understood that the dimensions given are illustrative and not intended to be limiting. It is clear that different dimensions may be used for the thickness of electrodes 16 and the spacing between the outer surface of electrodes 16 and lands 20.

The lead body 10 itself of lead 8 is made of a suitable insulating material of the type well known in the art. High quality, complex extrusions suitable for use in a multi-lumen lead may be created from a number of different polymers. Typically, polyurethane or silicone tubing has been most frequently used in body implantable stimulating and sensing leads. However, other thermoplastics and polymers such as nylon, polytetrafluoroethylene (PTFE) or the like might be adapted to such use. The particular insulating material used in construction of the lead itself is not important in the context of this invention so long as the material is a suitable biocompatible polymer that can function as an electrical insulator.

Figure 3:
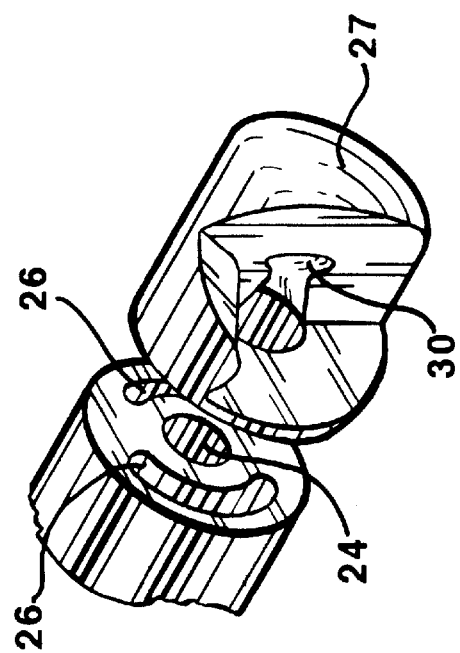
FIG. 3 shows a detail of the lead of FIG. 1 in the area designated by the numeral 3 and illustrates the multi-lumen character of the main lead body as well as the configuration of a preferred tip construction for such lead.
Figure 5:
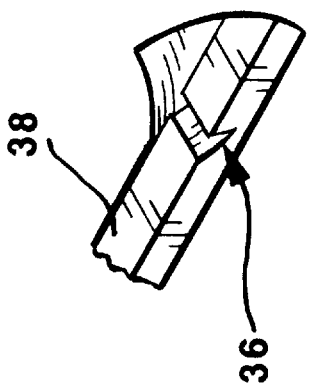
FIG. 5 shows a detail of the area 5 of FIG. 4 showing a semicircular hole which may be employed to accomplish the connection between a conductor and a ring electrode.

FIG. 3 shows a detail of the tip 22 of the lead construction and also illustrates a detail of the multi-lumen character of one embodiment of the lead body 10. In this embodiment, a central lumen 24 extends through lead 8 from proximal end 14 to distal end 12. Lumen 24 is co-axial with lead body 10 and is suitable for receiving a stiffening stylet (not shown) to run the length of the lead 8. The stiffening stylet stiffens the lead 8 during insertion and is intended to be removed after insertion and during use of lead 8.

In one embodiment, at least one additional lumen 26 may be added to lead 8 in addition to lumen 24. Lumen 26 may carry conducting wires 28 to electrodes 16 (FIGS. 6 and 7) or may be used to infuse or remove liquids from the distal end of lead 8. Conducting wires 28 extend from the connector block to the individual ring electrodes 16 at the distal end of the lead 8.

One type of conducting wire 28 that may be used is bundled stranded wire. Bundled stranded wire is a commercially available conductor which is a fine wire rope made of implantable conductive materials. Many different configurations of size, number and arrangements of strands are available from suitable manufacturers. For example, a suitable embodiment of bundled stranded wire preferred in the construction of this invention possesses seven individual strands, each strand having a diameter of 0.00133 inch to provide a seven stranded bundle having an outside diameter of 0.004 inch.

The bundle is twisted appropriately and provided with an insulated coating, for example, a one mil coating of polytetrafluoroethylene polymer. Such bundled stranded wire in accordance with this invention has a high degree of strength. The bundled and twisted nature of the wire provides a high degree of flex and crush resistance while maintaining flexibility and permitting the interconnection of as many as eight or more electrodes 16 at the distal end of a suitable lead 8 while maintaining a diameter less than approximately 0.053 inch.

In a preferred embodiment, two lumens 26 are formed on opposite sides of lumen 24. It may be desirable to form lumens 26 in an arcuate configuration to fit around lumen 24. Although the instant embodiment shows a tri-lumen lead with four conducting wires 28 in each of the opposite arcuate lumens 26, alternative constructions could be chosen such as having more than two lumens 26 in various shapes other than circular or arcuate.

Leads for neurological stimulation having any number of electrodes 16 may be built. It is believed that a configuration of four and as many as eight or more ring electrodes 16 may be desirable. In addition, it may be desirable to arrange the central lumen 26 in an asymmetrical position with respect to other of the lumens to obtain some advantage in steerability. In accord with this invention it is merely preferred to accommodate the conducting wires 28 in a lumen other than the stylet receiving central lumen 24 because of the bundled stranded wire nature of the conducting wires 28.

It is desirable to have a rounded tip on the distal end 12 of lead 8. Consequently, the distal end 12 of lead 8 may be integrally formed to the desired shape. Alternately, a tip 22 may be attached on the distal end 12 of the lead body 10. Tip 22 is preferably constructed of a biocompatible plastic similar to that forming the lead body 10 of lead 8.

In one embodiment, tip 22 has a central recess 30 that aligns with lumen 24. Tip 22 is then attached to lead 8 by means such as gluing with a biocompatible glue. In a preferred aspect of this invention, the distal interior portion of central recess 30 is configured to receive a ball tip stylet.

Such a ball shaped stylet is of the type already used in a Model 3888 lead sold by Medtronic, Inc. of Minneapolis, Minn. In use, the ball tip stylet (not illustrated) is advanced through lumen 24 until the ball enters central recess 30 of tip 22. The ball may then be frictionally engaged in central recess 30 thereby providing increased steerability and control of the lead 8 under certain implant circumstances.

FIG. 4 illustrates a ring electrode 16 prior to emplacement upon the lead 8. Electrode 16 is preferably provided as a "C" shaped strip of conducting electrode material. The preferred conducting material for electrode 16 is platinum iridium. Electrode 16 has an opening 32 slightly greater than the diameter of notches 18. As mentioned above, electrode 16 has a thickness less than the depth of notches 18.

Electrode 16 preferably has either a hole 34 or a slot 36 to connect electrode 16 to a conducting wire 28. Hole 34 may be formed in the side of electrode 16 by any technique well known in the industry. Alternately, a slot 36 may be formed in the opposing surfaces 38 of electrode 16 that are brought together as explained hereafter to form a ring shape. Slot 36 may be of any shape including but not limited to semicircular, "V" shaped or square.

It is not necessary for electrode 16 to have both hole 34 and slot 36 inasmuch as only a single electrical connection between conducting wire 28 and electrode 16 need be accomplished. The bare end of conducting wire 28 is passed either through hole 34 or is placed in slot 36.

With the conducting wire 28 in contact with electrode 16, the "C" shaped electrode 16 is placed over a notch 18 and is closed around notch 18 by means such as crimping so that opposing surfaces 38 are placed in an abutting relationship. As a result, electrode 16 forms a continuous ring around notch 18. It is preferable for the interior diameter of electrode 16 to be the same as the exterior diameter of notch 18 so that electrode 16 fits snugly around notch 18.

As described above, because electrode 16 has a thickness less than the difference in height between notches 18 and lands 20, the outer surface of electrode 16 will be recessed below the surface of lands 20. The Abutting opposing surfaces 38 of electrode 16 are then connected, preferably by means such as soldering or laser welding.

In either the embodiment of hole 34 or slot 36, conducting wire 28 is attached to electrode 16 by means such as soldering, laser welding or other means well known in the art. The connection of electrode 16 to conducting wire 28 through either hole 34 or slot 36 fully accomplishes the interconnection of electrode 16 with the conducting wire 28 and creates an electrical path from one contact at the connector block to electrode 16 at the distal end 12 of lead 8.

Other ways of connecting electrode 16 to conducting wire 28 can be envisioned such as using adhesives. However, providing a hole 34 or slot 36 in electrode 16 and attaching conducting wire 17 to electrode through hole 34 or slot 36 through techniques such as soldering or laser welding provides a convenient way to mate the electrode 16 with its conducting wire 28.

Electrodes 16 may also be attached to lead 8 in lands 20 by means other than crimping the "C" shaped electrode 16 around lead 8 as described above. For example, electrode 16 could be made by combining two conductive half-cylinders by laser welding or the like around lead body 10 to make a cylindrical electrode 16. Many other ways of making an electrode 16 that is recessed from the lands 20 will occur to those skilled in the art.

Figure 6:
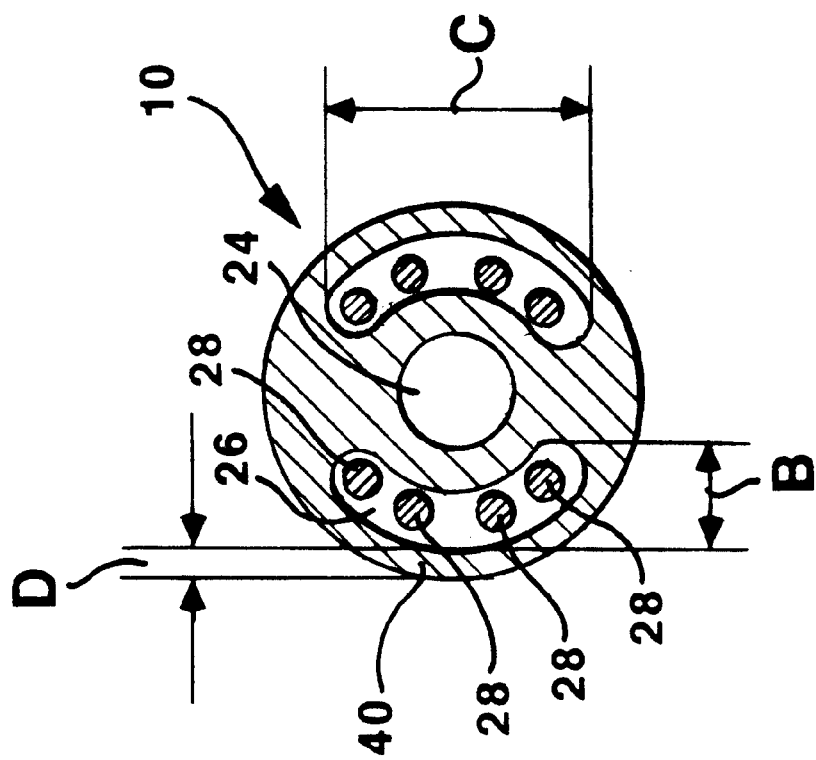
FIG. 6 is a cross sectional view of the body of the lead of FIG. 1 taken along line 6—6 illustrating the position of the conductors within two of the lumens of the lead and illustrating the dimension of a particular embodiment of a lead.

Referring now to FIG. 6, there is illustrated a sectional view of lead 8 taken along line 6—6 of FIG. 1. Line 6—6 extends through a land 20. This sectional view shows the two arcuate lumens 26 on opposite sides of the stylet receiving central lumen 24 in the embodiment described above. In an illustrative embodiment of the present invention, the overall diameter of lead 8 may be suitably provided as about 0.050 inch. The central lumen 24 in such an embodiment preferably has a diameter of about 0.013 inch. Lumens 26 may then have a width "B" of about 0.007 inch and a length "C" of about 0.030 inch.

A layer of insulation 40 surrounds lead body 10. This layer of insulation may the same material as and even integral with lead body 10. Alternately, insulation 40 may be a separate layer of material surrounding lead body 10. The thickness of the layer of insulation is labeled "D".

The minimum thickness D of insulation 40 is about 0.004 inch and the typical thickness D of insulation 40 is about from 0.005 to 0.006 inch. Accordingly, when the laser etching or milling is accomplished through this layer of insulation 40 to form notches 18, the depth of such notches 18 should be about the thickness of insulation 40 as will be explained hereafter. The foregoing dimensions are provided for illustrative purposes only and are not intended to limit the scope or spirit of this invention.

Figure 7:
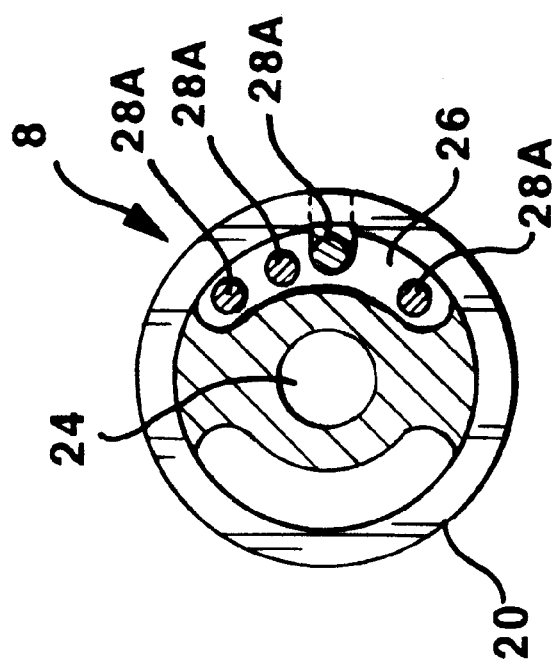
FIG. 7 is a cross-sectional view of the body of the lead of FIG. 1 taken along line 7—7.

FIG. 7 is a sectional view of lead 8 taken along line 7—7 in FIG. 1. Line 7—7 is in a region where a notch 18 has been formed. As shown, the insulation 40 has been removed a depth sufficient to expose lumens 26 so that one of the conducting wires 28A may be accessed and connected to the electrode 16 as described above.

It is anticipated that in some applications it may be desirable to place a lead 8 similar to the one described herein or a standard lead such as that disclosed in U.S. Pat. No. 4,379,462 issued to Borkan in side by side or overlapping relation. Because electrodes 16 are recessed from the surface of lands 20, contact between the leads will be on the insulating surface of lands 20. Electrodes 16 will be spaced from contact with any electrodes on the touching lead.

It is also anticipated that in some applications it may be desirable to place a lead such as the RESUME® "paddle" lead described above in side by side or overlapping contact with lead 8. As above, because electrodes 16 are recessed from the surface of lands 20, contact between the leads will be on the insulating surface of lands 20. Electrodes 16 will be spaced from contact with any electrodes on the touching lead.

Although in the embodiments disclosed the lead insulation has been notched or milled to accommodate the electrodes 16, it will be understood that the electrodes 16 could be placed directly over the lead 8 without notching the insulation 40. In that case, the electrodes 16 would be compression fitted around and into lead 8 to create the recessed configuration of the electrodes 16.

There has been described herein a body implantable medical lead and a process for placing ring electrodes on body implantable medical leads. Use of the inventions of this application provide a relatively inexpensive lead of high quality and having a resistance to shorting when the lead is brought into contact with another lead. While the invention herein has been described in connection with a particular embodiment, one skilled in the art will appreciate that numerous other embodiments and departures from the embodiment shown may be made without departing from the inventive concepts disclosed.

For example, the lead may be used in combination with a wide range or variety of tip constructions including conductive tips, particularly if the lead is adapted to a pacing application. A wide variety of dimensions for the elements such as the electrodes 16 and the lumens 26, 32 may be chosen. In addition other features may be added to the lead 8 while still employing the inventive elements herein. It is therefore to be understood that, within the scope of the appended claims, the invention maybe practiced in a fashion other than has been specifically described.

What is claimed is:

1. A body implantable lead comprising:
    a lead body having a central axis, proximal and distal ends and a lead body outer surface, the lead body having at least one notch formed in the outer surface of the lead body;
    at least one electrically conductive solid electrode spaced along the distal end of the lead body, each of the electrodes having an outer electrode surface, the outer surface of the electrode being located in a notch and recessed from the lead body outer surface, the electrode having a thickness;
    at least one contact located at the proximal end of the lead body; and
    at least one conductor connecting a respective one of the electrodes to a respective one of the contacts.

2. The lead of claim 1 wherein the at least one electrically conductive electrode is substantially annular.

3. The lead of claim 1 wherein the electrode is substantially cylindrically shaped.

4. The lead of claim 1 wherein the lead body has at least one recessed portion located at the distal end of the lead body, the recessed portion having a recess depth from the lead body outer surface that is greater than the thickness of the electrode, the electrode being located in the recessed portion;
    whereby the electrode is recessed from the lead body outer surface.

5. The lead of claim 4 wherein the electrode is substantially cylindrically shaped and fits around the recessed portion.

6. The lead of claim 1 wherein the at least one contact located at the proximal end of the lead body is part of a connector block.

7. The lead body of claim 1 wherein the lead body is made of an insulating material.

8. The lead of claim 7 wherein the insulating material is chosen from the group consisting of polymers and thermoplastics.

9. The lead of claim 1 wherein the lead body has a first lumen.

10. The lead of claim 9 wherein the at least one conductor is within the first lumen.

11. The lead of claim 9 wherein the first lumen is coaxial with the central axis of the lead body.

12. The lead of claim 9 wherein the first lumen is not coaxial with the central axis of the lead body.

13. The lead of claim 9 wherein the lead body has a second lumen.

14. The lead of claim 13 where the lead body has a third lumen.

15. The lead of claim 14 wherein the first lumen is coaxial with the central axis of the lead body and the second and third lumens are located on opposite sides of the first lumen.

16. The lead of claim 15 wherein the second and third lumens are arcuate shaped.

17. The lead of claim 9 wherein the first lumen is not coaxial with the central axis of the lead body and the second and third lumens are located on opposite sides of the first lumen.

18. The lead of claim 17 wherein the second and third lumens are arcuate shaped.

19. The lead of claim 1 wherein the distal end of the lead is rounded.

20. A body implantable lead comprising:
    a lead body having a central axis, proximal and distal ends and a lead body outer surface, the lead body having at least one recessed portion located at the distal end of the lead body, the lead body having at least one notch formed in the outer surface of the lead body;
    at least one electrically conductive substantially annular solid electrode spaced along the distal end of the lead body, each of the electrodes having a thickness, each of the electrodes having an outer electrode surface, the outer surface of the electrode being located in a notch and recessed from the lead body outer surface;
    means for providing electrical potential to at least one of the electrodes;
    wherein the recessed portion in the lead body has a recess depth from the lead body outer surface that is greater than the thickness of the electrode, the electrode being located in the recessed portion;
    whereby the electrode is recessed from the lead body outer surface.

21. The lead of claim 20 wherein the means for providing electrical potential to at least on of the electrodes comprises:
    at least one contact located at the proximal end of the lead body; and
    at least one conductor connecting a respective one of the electrodes to a respective one of the contacts.

22. The lead body of claim 20 wherein the lead body is made of an insulating material.

23. The lead of claim 22 wherein the insulating material is chosen from the group consisting of polymers and thermoplastics.

24. The lead of claim 20 wherein the lead body has a first lumen.

25. The lead of claim 24 wherein the means for providing electrical potential to at least on of the electrodes comprises:
    at least one contact located at the proximal end of the lead body; and
    at least one conductor connecting a respective one of the electrodes to a respective one of the contacts.

26. The lead of claim 25 wherein the at least one conductor is within the first lumen.

27. The lead of claim 24 wherein the first lumen is coaxial with the central axis of the lead body.

28. The lead of claim 24 wherein the first lumen is not coaxial with the central axis of the lead body.

29. The lead of claim 24 wherein the lead body has a second lumen.

30. The lead of claim 29 where the lead body has a third lumen.

31. The lead of claim 30 wherein the first lumen is coaxial with the central axis of the lead body and the second and third lumens are located on opposite sides of the first lumen.

32. The lead of claim 31 wherein the second and third lumens are arcuate shaped.

33. The lead of claim 30 wherein the first lumen is not coaxial with the central axis of the lead body and the second and third lumens are located on opposite sides of the first lumen.

34. The lead of claim 33 wherein the second and third lumens are arcuate shaped.

35. The lead of claim 20 wherein the distal end of the lead is rounded.

36. A body implantable lead comprising:
a lead body having proximal and distal ends and a lead body outer surface;
at least one electrically conductive substantially annular electrode spaced along the distal end of the lead body, each of the electrodes having an outer electrode surface and a discontinuity through a portion of each of the electrodes the discontinuity forming opposed surfaces on each of the electrodes at opposite ends of the discontinuity, the opposing surfaces of the electrodes abutting and being securely fixed to one another, the outer surface of the electrode being recessed from the lead body outer surface;
at least one contact located at the proximal end of the lead body; and
at least one conductor connecting a respective one of the electrodes to a respective one of the contacts.

37. The lead of claim 36 wherein the electrode is substantially cylindrically shaped.

38. The lead of claim 36 wherein the electrode is substantially cylindrically shaped.

39. The lead of claim 36 wherein the at least one contact located at the proximal end of the lead body is part of a connector block.

40. The lead body of claim 36 wherein the lead body is made of an insulating material.

41. The lead of claim 40 wherein the insulating material is chosen from the group consisting of polymers and thermoplastics.

42. The lead of claim 36 wherein the lead body has a first lumen.

43. The lead of claim 42 wherein the at least one conductor is within the first lumen.

44. The lead of claim 42 wherein the lead body has a central axis and the first lumen is coaxial with the central axis of the lead body.

45. The lead of claim 42 wherein the lead body has a central axis and the first lumen is not coaxial with the central axis of the lead body.

46. The lead of claim 42 wherein the lead body has a second lumen.

47. The lead of claim 46 where the lead body has a third lumen.

48. The lead of claim 47 wherein lead body has a central axis, the first lumen is coaxial with the central axis of the lead body and the second and third lumens are located on opposite sides of the first lumen.

49. The lead of claim 47 wherein the second and third lumens are arcuate shaped.

50. The lead of claim 47 wherein the lead body has a central axis, the first lumen is not coaxial with the central axis of the lead body and the second and third lumens are located on opposite sides of the first lumen.

51. The lead of claim 50 wherein the second and third lumens are arcuate shaped.

52. The lead of claim 36 wherein the distal end of the lead is rounded.

53. A body implantable lead comprising:
a lead body having a central axis, proximal and distal ends and a lead body outer surface, the lead body having at least one recessed portion located at the distal end of the lead body, the lead body being made of an insulating material, the lead body having a first lumen, the distal end of the lead being rounded, the lead body having at least one notch formed in the outer surface of the lead body;
at least one electrically conductive substantially annular solid electrode spaced along the distal end of the lead body, each of the electrodes having a thickness, each of the electrodes having an outer electrode surface, the outer surface of the electrode being located in a notch and recessed from the lead body outer surface;
at least one contact located at the proximal end of the lead body; and
at least one conductor connecting a respective one of the electrodes to a respective one of the contacts
wherein the recessed portion in the lead body has a recess depth from the lead body outer surface that is greater than the thickness of the electrode, the electrode being located in the recessed portion;
whereby the electrode is recessed from the lead body outer surface.

54. The lead of claim 53 wherein the first lumen is coaxial with the central axis of the lead body.

55. The lead of claim 53 wherein the first lumen is not coaxial with the central axis of the lead body.

56. The lead of claim 53 wherein the lead body has a second lumen.

57. The lead of claim 56 where the lead body has a third lumen.

58. The lead of claim 57 wherein the first lumen is coaxial with the central axis of the lead body and the second and third lumens are located on opposite sides of the first lumen.

59. The lead of claim 58 wherein the second and third lumens are arcuate shaped.

60. The lead of claim 57 wherein the first lumen is not coaxial with the central axis of the lead body and the second and third lumens are located on opposite sides of the first lumen.

61. The lead of claim 60 wherein the second and third lumens are arcuate shaped.

* * * * *